United States Patent [19]

Cardis

[11] Patent Number: 4,626,368

[45] Date of Patent: Dec. 2, 1986

[54] BENZOTRIAZOLE DERIVATIVES AND ORGANIC COMPOSITIONS CONTAINING SAME

[75] Inventor: Angeline B. Cardis, Florence, N.J.

[73] Assignee: Mobil Oil Corporation, New York, N.Y.

[21] Appl. No.: 807,425

[22] Filed: Dec. 10, 1985

[51] Int. Cl.$^4$ .............................................. C10M 1/10
[52] U.S. Cl. .................. 252/49.9; 548/257; 548/259
[58] Field of Search ............... 252/49.9, 32.5; 548/257, 259

[56] References Cited

U.S. PATENT DOCUMENTS

| | | | |
|---|---|---|---|
| 3,926,823 | 12/1975 | Durr et al. | 252/49.9 |
| 3,969,237 | 7/1976 | Andress, Jr. | 252/49.9 |
| 3,986,967 | 10/1976 | Okorodudu | 252/49.9 |
| 4,144,180 | 3/1979 | Andress, Jr. | 252/49.9 |
| 4,313,840 | 2/1982 | Komatsuzaki et al. | 252/49.9 |
| 4,376,635 | 3/1983 | Sung | 548/257 |
| 4,378,361 | 3/1983 | Schruman et al. | 548/257 |
| 4,519,928 | 5/1985 | Braia | 252/50 |
| 4,532,057 | 7/1985 | Horoaysky et al. | 558/83 |

*Primary Examiner*—William R. Dixon, Jr.
*Assistant Examiner*—Cynthia A. Prezlock
*Attorney, Agent, or Firm*—Alexander J. McKillop; Michael G. Gilman; Howard M. Flournoy

[57] ABSTRACT

Benzotriazole or a substituted benzotriazole when reacted with alkyl aldehydes and dialkylhydrogen phosphites provide products which improve the load-carrying, antiwear properties of lubricant oils and greases.

15 Claims, No Drawings

BENZOTRIAZOLE DERIVATIVES AND ORGANIC COMPOSITIONS CONTAINING SAME

BACKGROUND OF THE INVENTION

Benzotriazole and its derivatives are known lubricant additives. U.S. Pat. No. 4,519,928 discloses the use of N-t-alkylated benzotriazoles to impart oxidation and corrosion resistance properties to lubricants. Benzotriazole and its derivatives are also known to impart copper deactivation to luricants. Limited oil solubility is a problem, however, Organophosphorus compounds have been used to improve the load-carrying ability of lubricants as well as to improve their oxidative stability. Further, U.S. Pat. No. 4,532,057 discloses hydrogen phosphite reaction products as friction modifiers in lubricants and fuels.

Products are known which are the reaction product of a phosphorus acid with a benzotriazole to form an amine phosphate, or which are the reaction product of a phosphorochloridate (-ite) with a benzotriazole to give a product which contains a P-N bond. However, no reference discussed above or known to applicant discloses the benzotriazole derivatives of this invention, e.g., benzotriazolylmethyl phosphonates or phosphates as lubricant additives.

SUMMARY OF THE INVENTION

It has now been discovered that benzotriazole and substituted benzotriazoles, when reacted with hydrocarbyl aldehydes and hydrocarbyl phosphites give oil soluble products which improve load carrying and antiwear properties of lubricant oils and greases. This invention is, therefore, more specifically directed to lubricant compositions comprising a major amount of an oil of lubricating viscosity or grease prepared therefrom and a minor load-carrying/antiwear amount of a product of reaction obtained by reacting a hydrocarbyl aldehyde, a dihydrocarbyl phosphite and a benzotriazole and to said products of reaction.

DESCRIPTION OF PREFERRED EMBODIMENTS

The load-carrying/antiwear additives of the present invention are products of reaction preferably derived from the reaction of benzotriazole or a substituted benzotriazole, a $C_1$ to about a $C_8$ alkyl aldehyde and a dialkylhydrogen phosphite having from 1 to about 30 carbon atoms per alkyl moiety.

The reaction is generally carried out in substantially equimolar amounts, at temperatures of from about 70° to about 120° C. under ambient pressure, although higher pressures may be used if desired. Temperatures of from about 70° to about 120° C. are usually used with temperatures of from about 80° to about 110° C. being preferred. Reaction time varies from about 3 to about 8 hours or more depending on reactants and reaction parameter.

Although the reactants are preferably used in equimolar amounts a 10% excess of the phosphite and aldehyde may be employed to insure complete reaction of the benzotriazole.

Solvents may be used if thought desirous. Suitable solvents include pentane, cyclohexane, heptane, octane, nitrobenzene, trifluoromethyl benzene, perfluoromethyl benzene, ethanol, butanol, other alcohols, or mixtures of such solvents and the like. N-heptane is often preferred.

The benzotriazole compounds which are utilized in the present invention as reactants have the generalized formula:

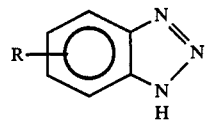

where R is hydrogen or hydrocarbyl containing from 1 to about 12 carbon atoms, and preferably is hydrogen or an alkyl group containing from 1 to about 8 carbon atoms. Particularly preferred are benzotriazole and toluotriazole.

Aldehydes utilized in the present invention as reactants have the following generalized formula:

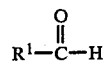

wherein $R^1$ is selected from hydrogen and hydrocarbyl, preferably alkyl radicals containing from 1 to about 8 carbon atoms. Examples of suitable aldehydes include formaldehyde, acetaldehyde, propanaldehyde, butrylaldehyde, hexaldehyde and heptaldehyde. The most preferred aldehyde reactant is formaldehyde, which may be used in its monomeric or its polymeric form, such as paraformaldehyde.

Dihydrocarbyl phosphites utilized herein as reactants have the following generalized formula.

$$(R^2O)_2POH$$

$R^2$ may be the same or different and is a hydrocarbyl group preferably alkyl containing from 1 to about 30 carbon atoms, but may be aryl or alkylated aryl. The phosphites include, but are not limited to, those wherein $R^2$ is methyl, ethyl, propyl, butyl, pentyl, hexyl, 2-ethylhexyl, lauryl, oleyl, phenyl, nonylphenyl and the like.

The additives in accordance with the present invention improve the load-carrying/antiwear properties of various lubricating media. These preferably comprise liquid oils, in the form of either a mineral oil or a synthetic oil or mixtures thereof, but also may be a grease in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SUS at 100° F. to about 6000 SUS at 100° F., and preferably, from about 50 to about 250 SUS at 210° F. These oils may have viscosity indexes ranging to about 100 or higher. Viscosity indexes from about 70 to about 95 are preferred. The average molecular weights of these oils may range from about 250 to about 800.

Where the lubricant is to be employed in the form of a grease, the lubricating oil is generally employed in an amount sufficient to balance the total grease composition, after accounting for the desired quantity of the thickening agent and other additive components to be included in the grease formulation. A wide variety of materials may be employed as thickening or gelling agents. These may include any of the conventional metal salts or soaps, which are dispersed in the lubricating vehicle in greaseforming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, phenoxy phenylethers.

In general, the additive reaction products of the present invention may be employed in any amount which is effective for imparting the desired degree of load carrying/antiwear improvement. In many applications, however, the additive is effectively employed in amounts from 0.01 to 10% by weight, preferably from about 0.1 to 5% of the total weight of the composition.

It is to be understood that the compositions contemplated herein can also contain other materials. For example, other corrosion inhibitors, extreme pressure agents, antiwear agents, defoamants, detergents, dispersants, and the like can be used. These materials do not detract from the value of the compositions of this invention. Rather the materials serve to impart their customary properties to the particular compositions in which they are incorporated.

The following examples will serve to illustrate but not limit the invention.

EXAMPLE 1

Dibutyl hydrogen phosphite (194g, 1.0 mole) and tolutriazole (133g, 1.0 mole) were stirred in 100 cc n-heptane under an atmosphere of nitrogen at 78°–80° C. as paraformaldehyde (33g, 1.1 moles) was added in portions over one hour. After an additional hour at 80° C., the temperature was raised to 98° C. and the solution was allowed to reflux for one hour. Solvent and volatiles were removed under reduced pressure (approximately 15 mm Hg) with a final temperature of 110° C. The product was cooled to 70° C. and filtered through a mat of diatomaceous earth.

The same procedure was followed substituting for dibutyl hydrogen phosphite an equal molar amount of di-(2-ethyl hexyl) hydrogen phosphite (Example 2), dilauryl hydrogen phosphite (Example 3), or di-oleyl hydrogen phosphite (Example 4) as referenced in Table 1 below.

TABLE 1

| Example | (RO)$_2$POH R | Product % P | % N |
|---|---|---|---|
| 1 | butyl | 8.59 | 10.84 |
| 2 | 2-ethyl hexyl | 6.74 | 8.10 |
| 3 | lauryl | 5.52 | 6.70 |
| 4 | oleyl | 3.84 | 5.50 |

Evaluation of Products

Selected products described hereinabove were blended in an 80/20 mixture of a 150 second solvent paraffinic bright mineral oil and a 200 second solvent paraffinic neutral mineral oil and tested in the Shell Four-Ball Wear Test. The results in Table 2 demonstrate the antiwear protection afforded by these products. The indicated additives were evaluated using ½ in. 52100 Steel Balls at a load of 60 kg and for 30 minutes under the conditions set forth in Table 2 below. In general, in this test three steel balls of 52–100 steel are held in a ball cup. A fourth ball positioned on a rotatable vertical axis is brought into contact with the three balls and is rotated against them. The force with which the fourth ball is held against the three stationary balls may be varied according to a desired load. The test lubricant is added to the ball cup and acts as a lubricant for the rotation. At the end of the test, the steel balls are investigated for wearscar; the extent of scarring represents the effectiveness of the lubricant as an antiwear agent.

TABLE 2

FOUR-BALL WEAR TEST SCAR DIAMETER (MM)
HALF-INCH BALLS, 52100 STEEL, 60 KG, 30 MIN.

| Additive | Conc. Wt. % | Temp °F. | Speed (RPM) 1500 | 2000 |
|---|---|---|---|---|
| Base Stock | 100 | 200 | 1.8 | 2.0 |
|  |  | 390 | 2.4 | 2.2 |
| Example 2 | 1 | 200 | 0.6 | 0.7 |
|  |  | 390 | 0.8 | 0.8 |
| Example 3 | 1 | 200 | 0.55 | 0.55 |
|  |  | 390 | 0.65 | 0.7 |
| Example 4 | 1 | 200 | 0.55 | 2.45 |
|  |  | 390 | 0.6 | 2.1 |

The product of Example 3 was added at a concentration of 0.20 wt. % to a fully formulated gear oil (A) and the Timken OK load was determined. The results in Table 3 demonstrate the improvement in EP load-carrying performance achievable with the products described herein.

The Timken Load Test - ASTM D2782 is summarized as follows: It determines the load carrying capacity of lubricating fluids by means of the Timken extreme pressure tester. The tester is operated with a steel test cup rotating against a steel test block. The rotating speed is 800+5 rpm. Fluid samples are preheated to 37.8°+2.8° C. before starting the test. Timken OK load is the maximum load value at which the rotating cup will not rupture the lubricant film and cause scoring or seizure between the rotating cup and the stationary block.

TABLE 3

| Test Oil | OK Load (kg) |
|---|---|
| Gear Oil A | 55, 50 |
| Gear Oil A + 0.2% Ex. 3 | 65, 65 |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A lubricant composition comprising a major amount of an oil of lubricating viscosity or grease prepared therefrom and a minor load-carrying/antiwear amount of a product of reaction obtained by reacting a $C_1$–$C_8$ hydrocarbyl aldehyde and a dihydrocarbyl phosphite having from 1 to about 30 carbon atoms in each hydrocarbyl moiety with a benzotriazole having the following generalized structural formula:

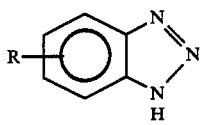

where R is H or hydrocarbyl having from 1 to about 12 carbon atoms, the reaction being carried out under ambient pressure at from about 70° to about 120° C. in substantially molar ratios of reactants.

2. The composition of claim 1 in which said aldehyde is an alkyl aldehyde and said phosphite is a dialkyl hydrogen phosphite.

3. The composition of claim 2 in which the benzotriazole is tolutriazole.

4. The composition of claim 3 in which the aldehyde is paraformaldehyde and the phosphite is dibutyl hydrogen phosphite.

5. The composition of claim 3 in which the aldehyde is paraformaldehyde and the phosphite is di-(2-ethylhexyl) hydrogen phosphite.

6. The composition of claim 2 in which the phosphite is dilauryl hydrogen phosphite.

7. The composition of claim 2 in which the phosphite is dioleyl hydrogen phosphite.

8. The composition of claim 1 in which the oil of lubricating viscosity is selected from mineral oils, synthetic oils and mixtures thereof.

9. The composition of claim 1 in which said major amount is a grease.

10. The composition of claim 1 in which said minor amount is at least about 0.1 wt. % based on the total weight of the composition.

11. A lubricant additive product of reaction obtained by reacting a $C_1$–$C_8$ alkyl aldehyde and a dialkyl hydrogen phosphite having from 1 to about 30 carbon atoms per alkyl moiety with benzotriazole having the following generalized structural formula:

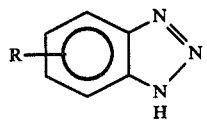

where R is H or hydrocarbyl having from 1 to about 12 carbon atoms, the reaction being carried out under ambient pressure at from about 70° to about 120° C. in substantially molar ratios of reactants.

12. The product of claim 11 in which the reactants are selected from paraformaldehyde, dibutyl hydrogen phosphite and tolutriazole.

13. The product of claim 11 in which the reactants are selected from paraformaldehyde, di-(2 ethylhexyl) hydrogen phosphite and tolutriazole.

14. The product of claim 11 in which the phosphite is selected from dilauryl hydrogen phosphite.

15. The product of claim 11 in which the phosphite is selected from dioleyl hydrogen phosphite.

* * * * *